(12) United States Patent
Malanowski et al.

(10) Patent No.: US 12,702,501 B2
(45) Date of Patent: Aug. 11, 2026

(54) ENDOSCOPE AND MOUNTING SYSTEM FOR A ROBOTIC SURGICAL SYSTEM

(71) Applicant: Auris Health, Inc., Redwood City, CA (US)

(72) Inventors: Samuel J. Malanowski, Menlo Park, CA (US); Theodore Leclere, San Francisco, CA (US); Juan B. Bajana Merizalde, San Francisco, CA (US); Alexander Tarek Hassan, San Francisco, CA (US); Fabien Y. Schmitt, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 557 days.

(21) Appl. No.: 18/191,777

(22) Filed: Mar. 28, 2023

(65) Prior Publication Data

US 2023/0240770 A1 Aug. 3, 2023

Related U.S. Application Data

(63) Continuation of application No. PCT/IB2021/060761, filed on Nov. 19, 2021.

(Continued)

(51) Int. Cl.
*A61B 34/30* (2016.01)
*A61B 1/00* (2006.01)

(52) U.S. Cl.
CPC ............ *A61B 34/30* (2016.02); *A61B 1/0004* (2022.02); *A61B 1/00105* (2013.01);

(Continued)

(58) Field of Classification Search
CPC .............. A61B 1/0004; A61B 1/00105; A61B 1/00149; A61B 34/30; A61B 1/00114; A61B 1/00117; A61B 2034/301
See application file for complete search history.

(56) References Cited

U.S. PATENT DOCUMENTS 5,702,349 A * 12/1997 Morizumi .......... A61B 1/00066 600/131
5,876,325 A * 3/1999 Mizuno .................. A61B 34/37 600/117

(Continued)

FOREIGN PATENT DOCUMENTS

CN 110772211 A 2/2020
EP 0392718 A2 10/1990

(Continued)

OTHER PUBLICATIONS

Written Opinion and International Search Report from PCT Application No. PCT/IB2021/060761 mailed Apr. 20, 2022.

*Primary Examiner* — Aaron B Fairchild
(74) *Attorney, Agent, or Firm* — Vorys, Sater, Seymour and Pease LLP

(57) ABSTRACT

Robotics surgical systems, instrument mounts, and endoscopes are disclosed. A robotic surgical system includes a robotic arm, an instrument mount arranged at a distal end of the robotic arm, and an endoscope comprising a housing and a shaft. The housing is configured to be mounted to the instrument mount, and the shaft extends from the housing in a distal direction. A cable is connected to the housing and extends from the housing in a distal direction and along a lateral side of the housing.

8 Claims, 18 Drawing Sheets

Related U.S. Application Data

(60) Provisional application No. 63/116,067, filed on Nov. 19, 2020.

(52) U.S. Cl.
CPC ...... *A61B 1/00114* (2013.01); *A61B 1/00117* (2013.01); *A61B 1/00149* (2013.01); *A61B 1/00119* (2013.01); *A61B 2034/301* (2016.02)

(56) References Cited

U.S. PATENT DOCUMENTS 6,451,027 B1 * 9/2002 Cooper .............. A61B 1/00149 901/19
6,520,908 B1 * 2/2003 Ikeda ................. A61B 1/00066 600/110
2002/0072653 A1 * 6/2002 Ishizuka ................ A61B 1/125 600/101
2004/0049205 A1 * 3/2004 Lee ........................ A61B 34/37 606/130
2005/0272975 A1 12/2005 McWeeney et al.
2009/0287043 A1 * 11/2009 Naito ..................... A61B 34/70 600/104
2016/0331214 A1 * 11/2016 Fujitani ................ A61B 1/0052
2017/0231686 A1 * 8/2017 Sartor .................. A61B 18/149 606/46
2019/0365402 A1 12/2019 Sholev et al.
2020/0094001 A1 3/2020 Orphanos
2020/0281667 A1 9/2020 Blondel et al.
2021/0298574 A1 * 9/2021 Takahashi .......... A61B 1/00002

FOREIGN PATENT DOCUMENTS

WO 2016168673 A1 10/2016
WO 2019139941 A1 7/2019

* cited by examiner 2104
1802
1604
1606
1608

2104
1802
1604
1606
1608

2104
1802
1604
1606
1608

ENDOSCOPE AND MOUNTING SYSTEM FOR A ROBOTIC SURGICAL SYSTEM

BACKGROUND

Minimally invasive procedures are often preferred over traditional open surgery due to the reduced post-operative recovery time and minimal scarring. In minimally invasive procedures, elongate medical instruments may be inserted into the patient through a small incision or natural orifice to visualize or manipulate tissue for diagnostic or therapeutic purposes. Robotic systems have recently been developed to assist in minimally invasive procedures, where the instruments are controllably manipulated by robot arms to access internal anatomical sites.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
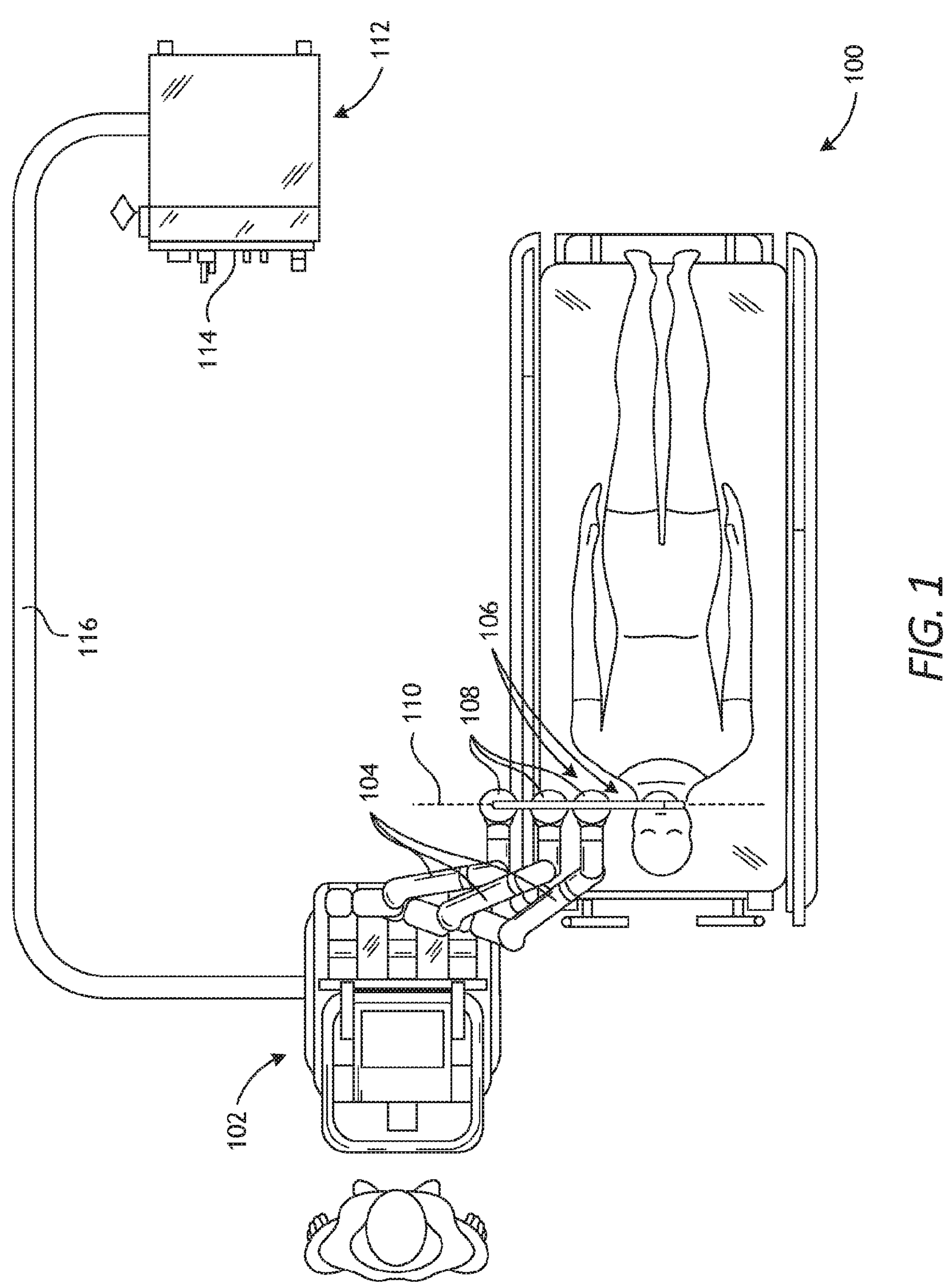
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 or connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
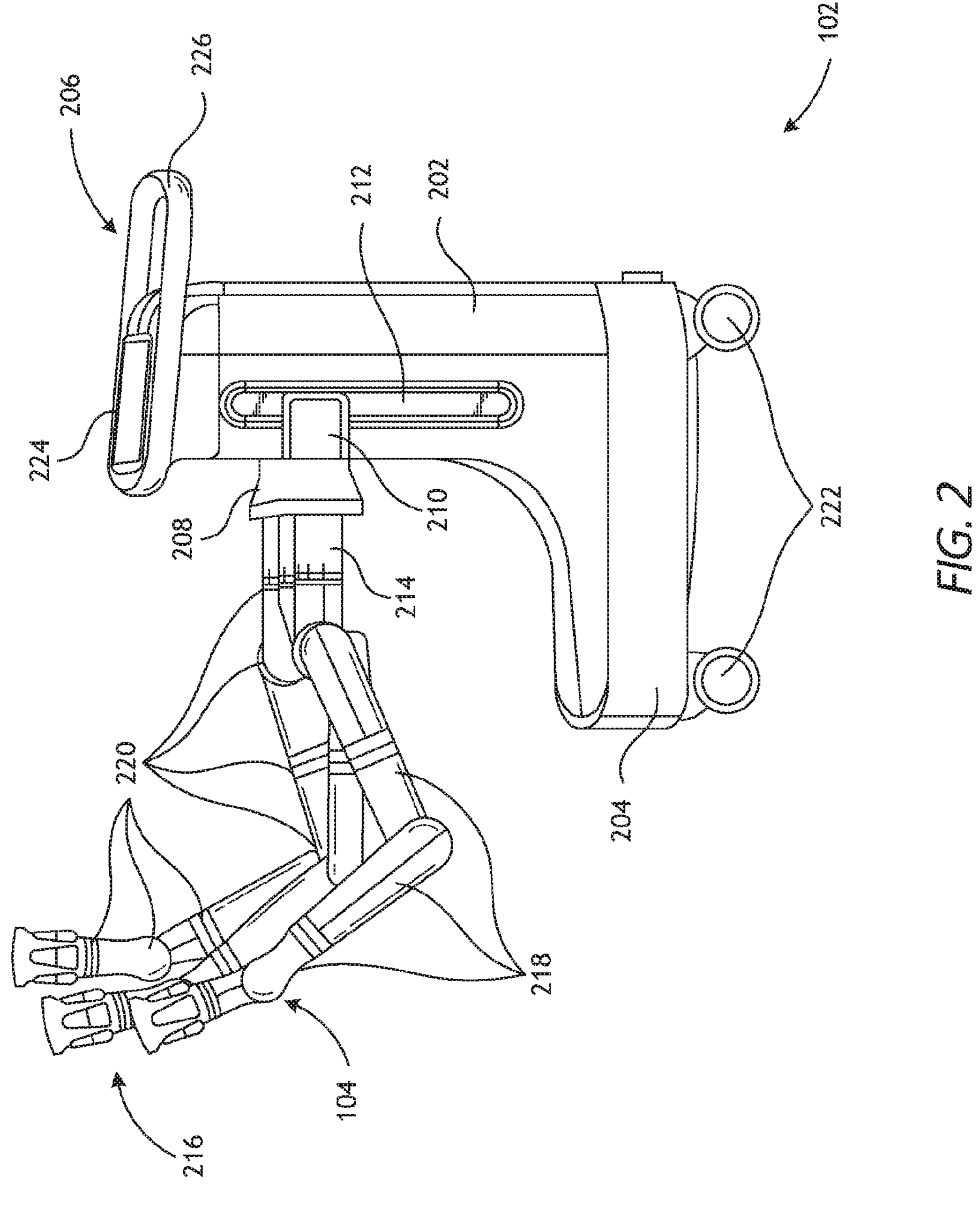
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively referred to as an "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots 212 provided on opposite sides of the column 202 to guide the vertical translation of the carriage 208. The slot(s) 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may comprise internal mechanisms, such as gears and motors, that are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, carriage 208, and arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing the cart 102.

Figure 3A:
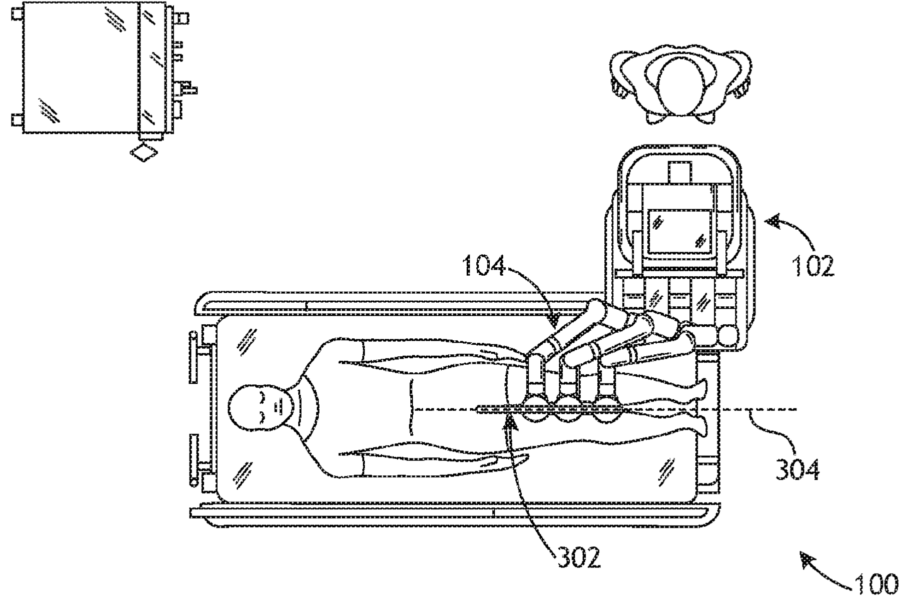
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
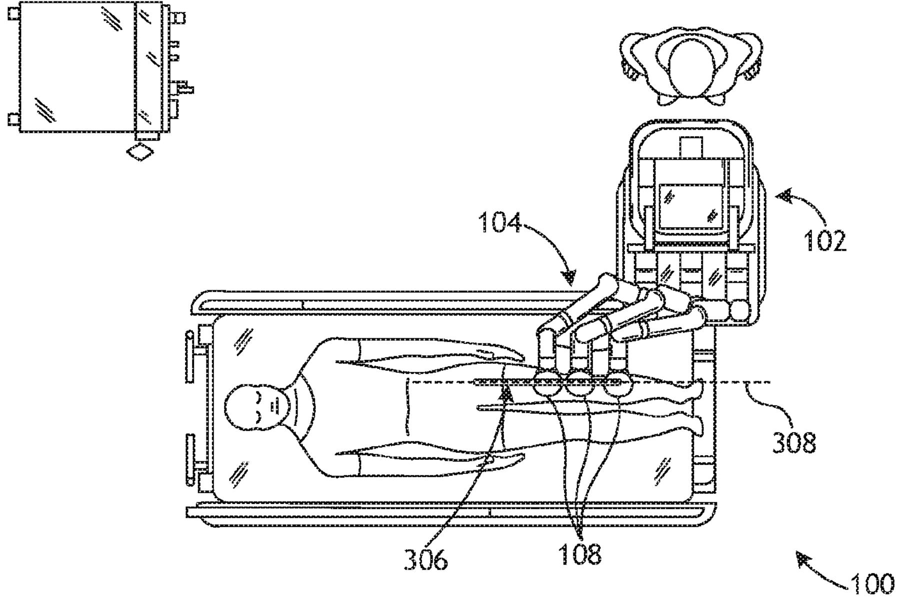
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
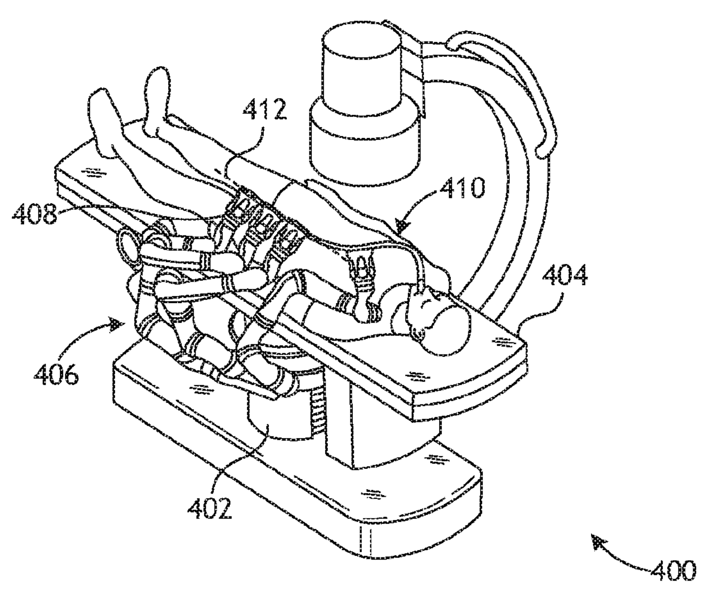
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
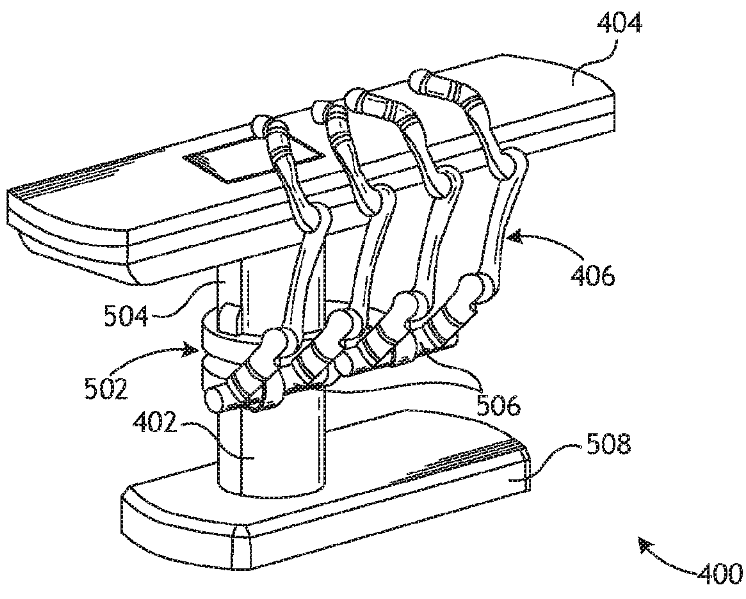
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages 502, and motors to mechanize the translation of said carriages based on the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
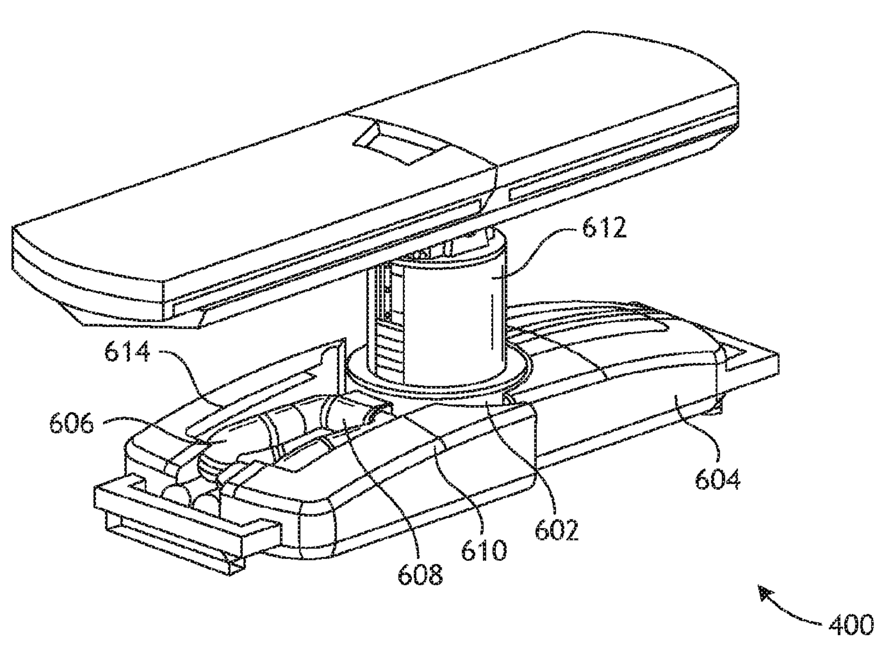
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
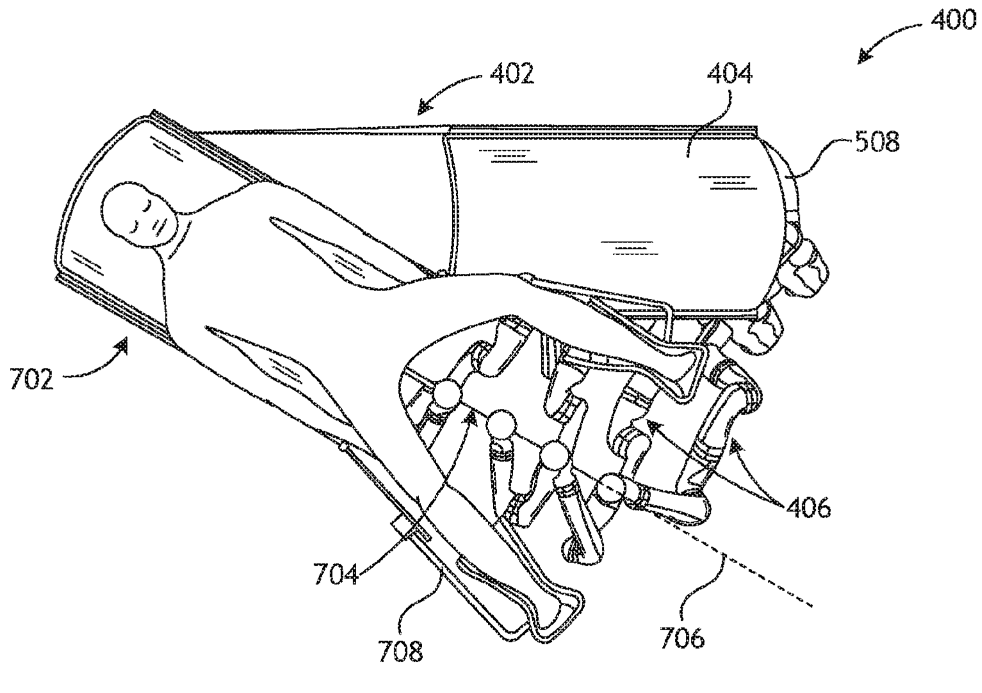
FIG. 7A illustrates an embodiment of a table-based robotic system configured for a ureteroscopy procedure.
Figure 7B:
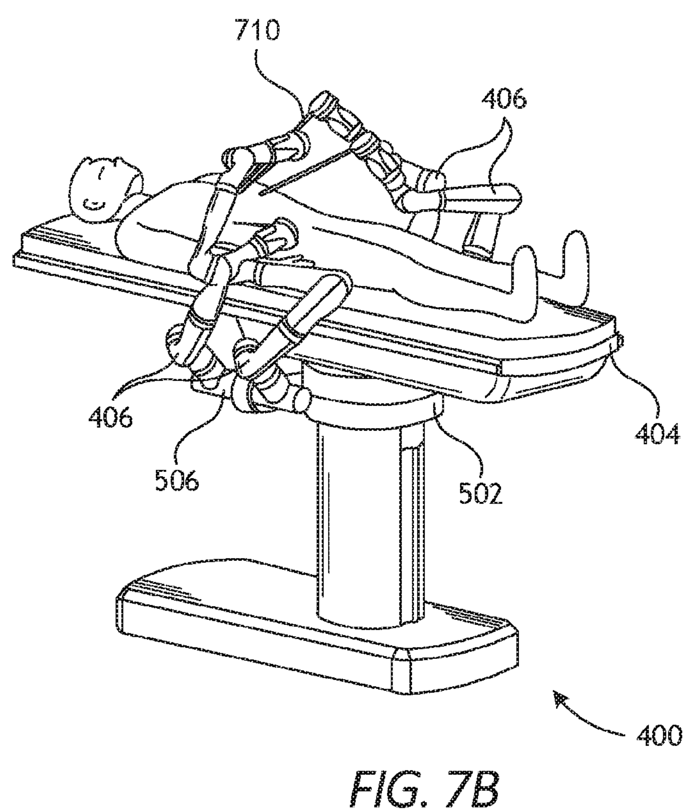
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
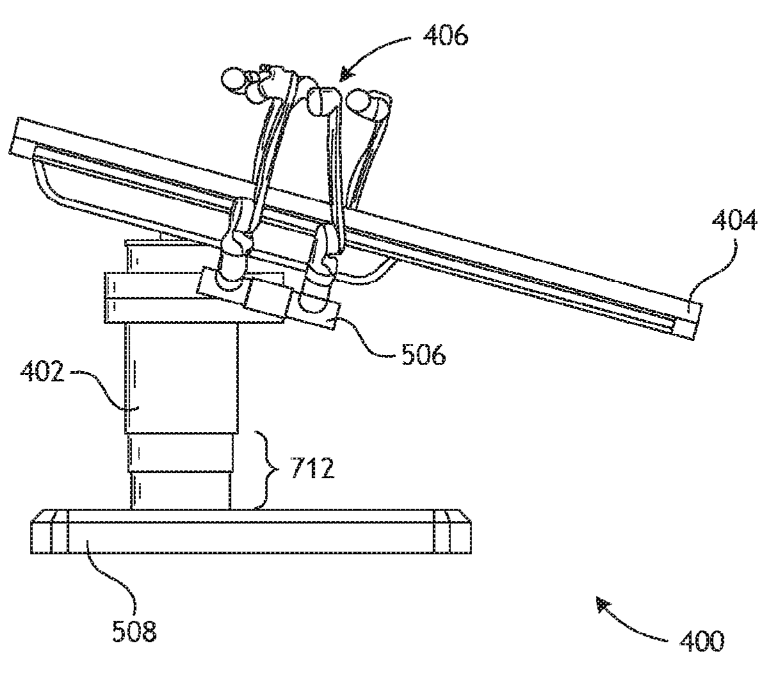
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
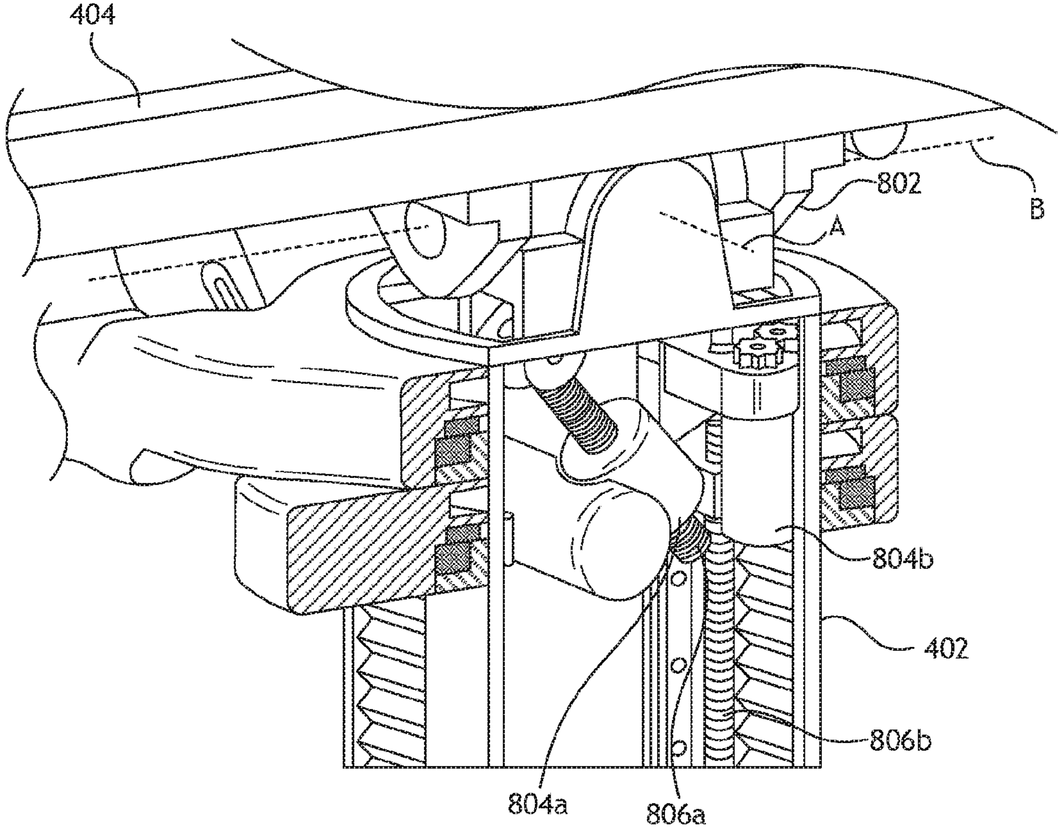
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804*a* and 804*b* responsive to an electrical pitch angle command. Rotation along one screw 806*a* would enable tilt adjustments in one axis A, while rotation along another screw 806*b* would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figures 9A, 9B:
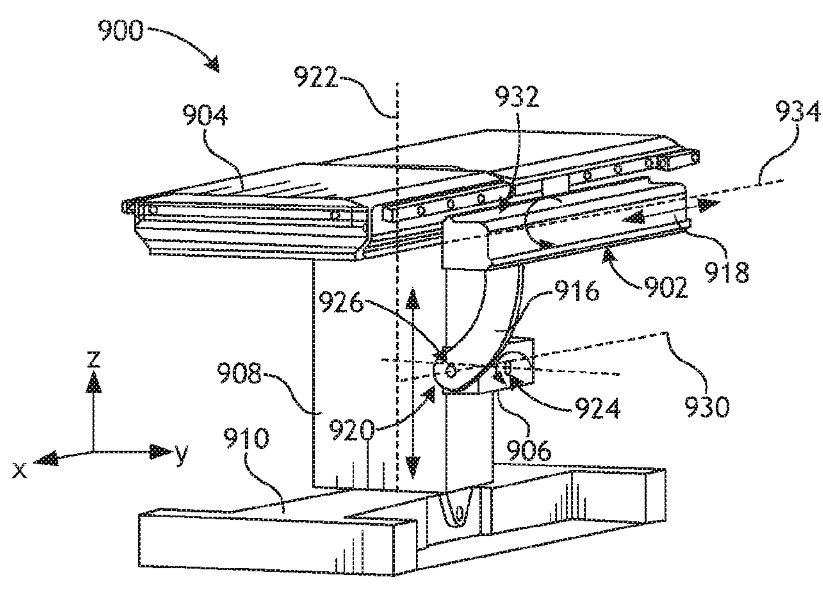
FIG. 9A illustrates an alternative embodiment of a table-based robotic system.
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by the column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include the carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B)

can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
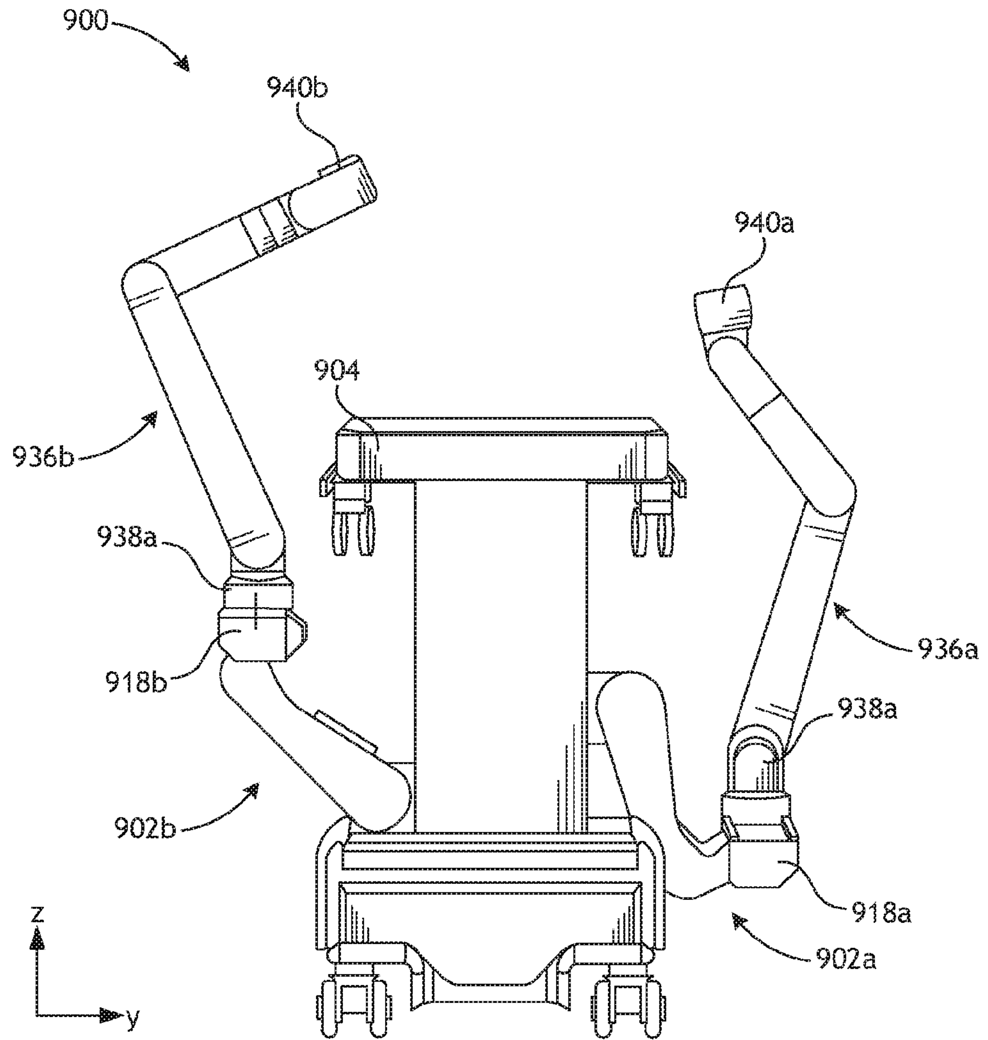
FIG. 9C illustrates an end view of a table-based robotic system with robotic arms attached thereto.

FIG. 9C illustrates an end view of the surgical robotics system 900 with two adjustable arm supports 902*a* and 902*b* mounted on opposite sides of the table 904. A first robotic arm 936*a* is attached to the first bar or rail 918*a* of the first adjustable arm support 902*a*. The first robotic arm 936*a* includes a base 938*a* attached to the first rail 918*a*. The distal end of the first robotic arm 936*a* includes an instrument drive mechanism or input 940*a* that can attach to one or more robotic medical instruments or tools. Similarly, the second robotic arm 936*b* includes a base 938*a* attached to the second rail 918*b*. The distal end of the second robotic arm 936*b* includes an instrument drive mechanism or input 940*b* configured to attach to one or more robotic medical instruments or tools.

In some embodiments, one or more of the robotic arms 936*a,b* comprises an arm with seven or more degrees of freedom. In some embodiments, one or more of the robotic arms 936*a,b* can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938*a,b* (1-degree of freedom including translation). In some embodiments, the insertion degree of freedom can be provided by the robotic arm 936*a,b*, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
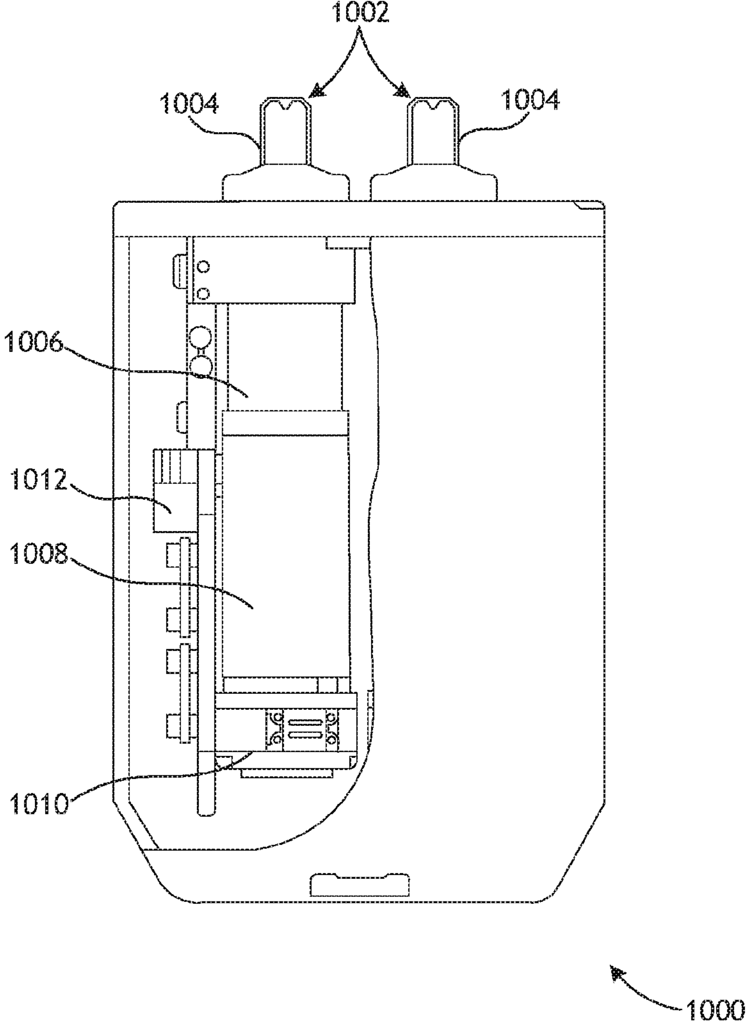
FIG. 10 illustrates an exemplary instrument driver.

FIG. 10 illustrates an example instrument driver 1000, according to one or more embodiments. Positioned at the distal end of a robotic arm, the instrument driver 1000 comprises one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape comprised of a thin, flexible material, such as transparent or translucent plastic, is designed to cover the capital equipment, such as the instrument driver 1000, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
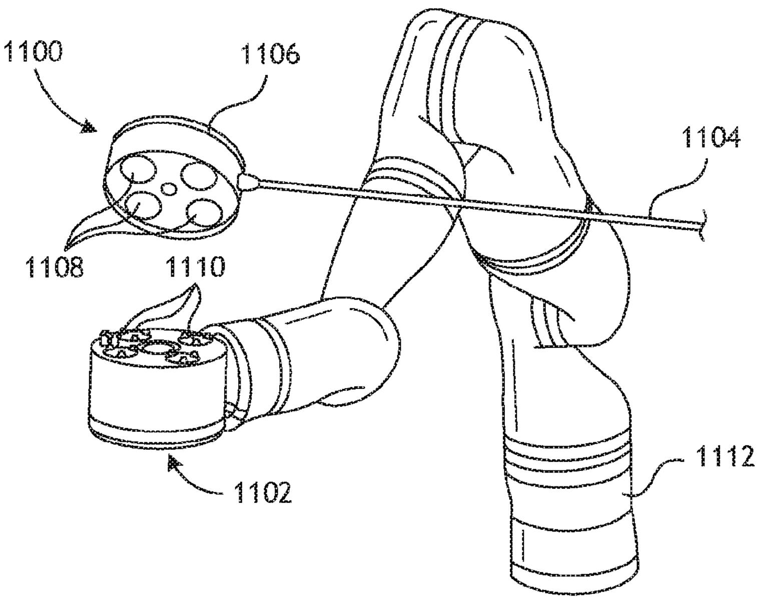
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon causes the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
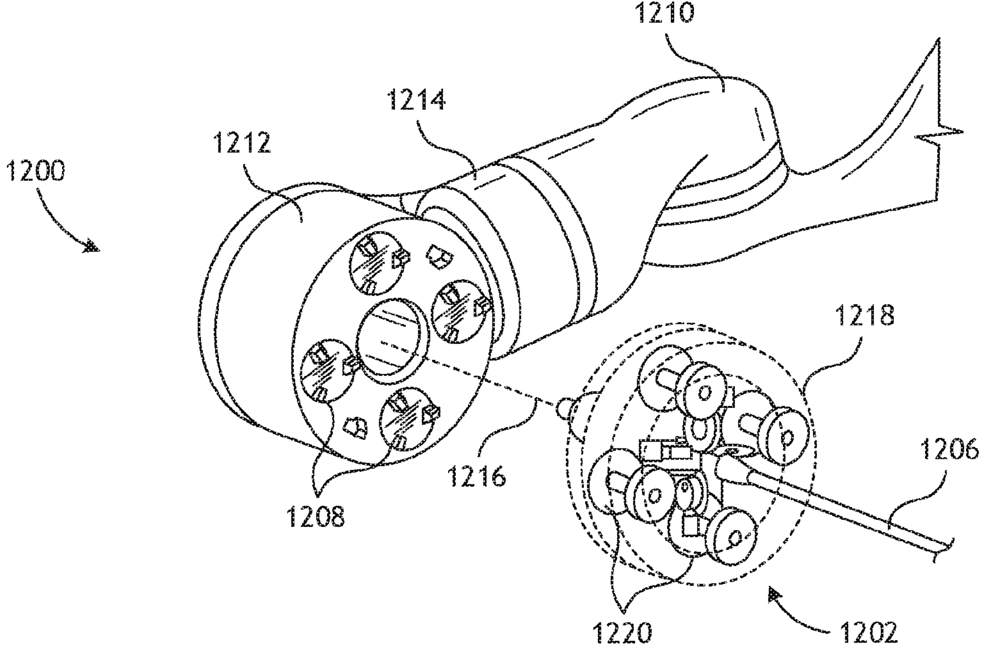
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
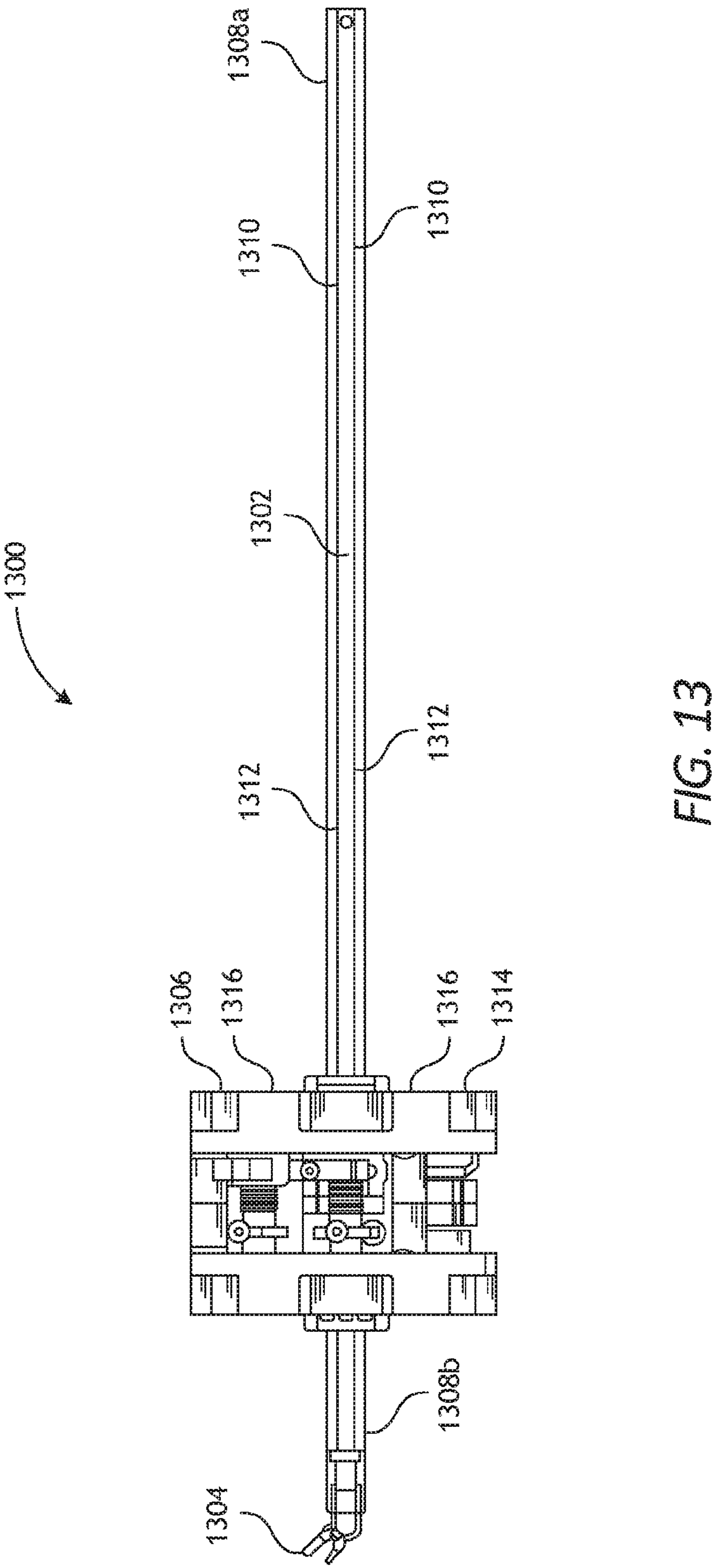
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308*a* and a distal portion 1308*b*. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
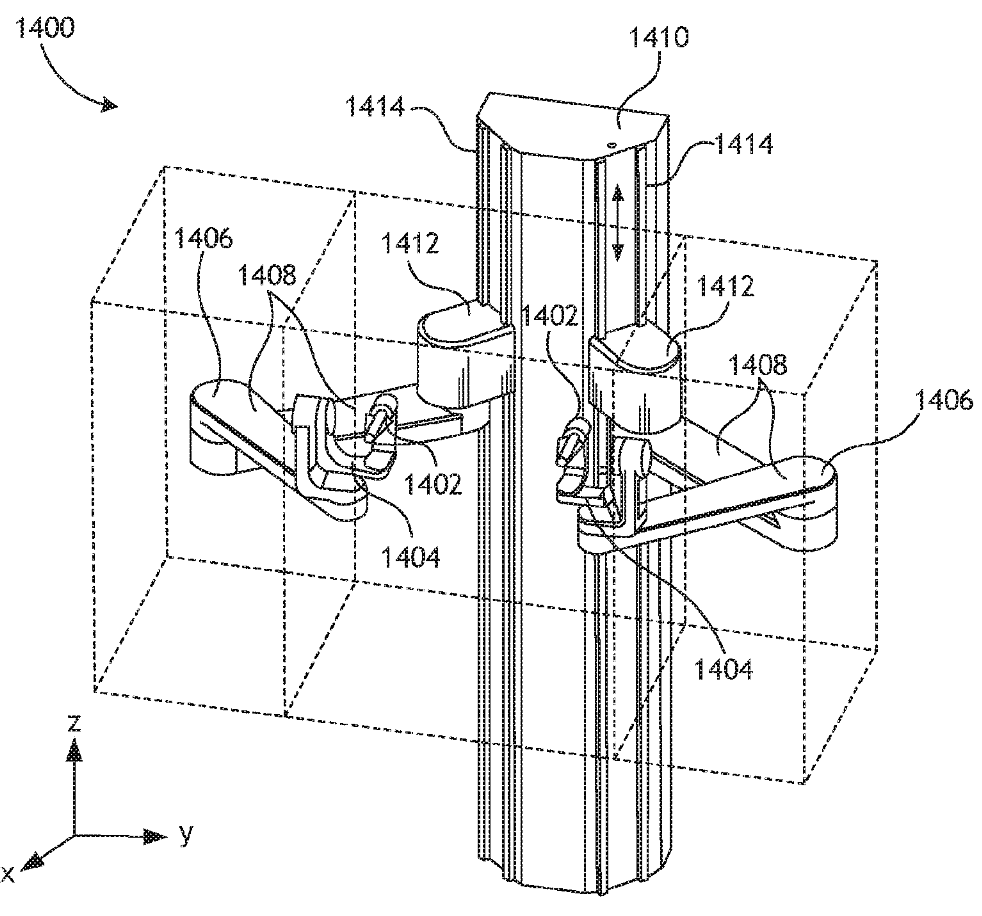
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
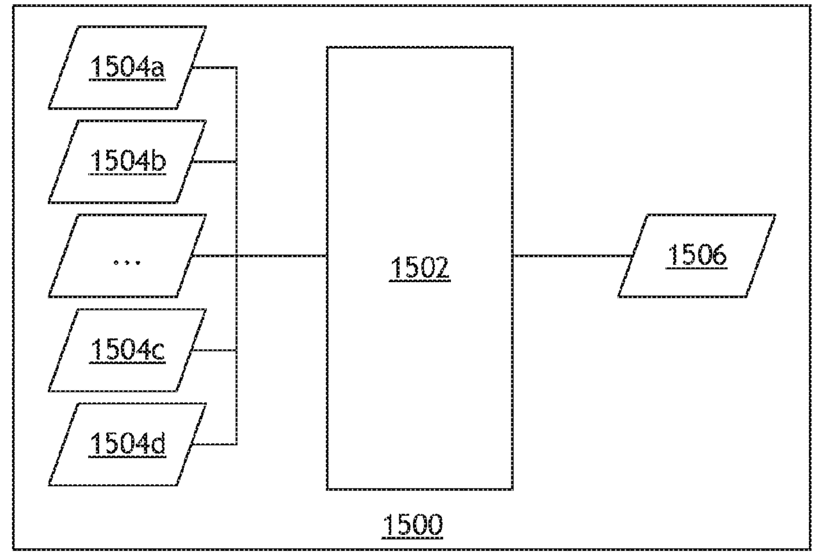
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504*a*, 1504*b*, 1504*c*, and 1504*d* to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504*a*-*d* are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504*a* (also referred to as "preoperative model data" when generated using only preoperative CT scans). The use of center-line geometry is discussed in U.S. Pat. No.

9,763,741, the contents of which are hereby incorporated by reference in their entirety. Network topological models may also be derived from the CT-images, and are particularly appropriate for bronchoscopy.

In some embodiments, the instrument may be equipped with a camera to provide vision data 1504*b*. The localization module 1502 may process the vision data 1504*b* to enable one or more vision-based location tracking. For example, the preoperative model data may be used in conjunction with the vision data 1504*b* to enable computer vision-based tracking of the medical instrument (e.g., an endoscope or an instrument advance through a working channel of the endoscope). For example, using the preoperative model data 1504*a*, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504*a* that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504*b* to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504*c*. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504*d* may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504*a-d* in combination(s). In some cases, such a combination may use a probabilistic approach where the localization module 1502 assigns a confidence weight to the location determined from each of the input data 1504*a-d*. Thus, where the EM data 1504*c* may not be reliable (as may be the case where there is EM interference) the confidence of the location determined by the EM data 1504*c* can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Endoscope and Mounting System.

Embodiments disclosed herein provide an endoscope and a mounting system that may be used to mount an endoscope or other medical instrument to a robotic surgical system.

Different instruments may present different considerations with respect to, for example, their use cases, cost, and durability requirements. By way of example, endoscopes may be used for initial port placement and at other times for manual exploration and visualization. Manual manipulation of the instrument makes it desirable to have a convenient way to attach and detach the instrument from the robotic instrument driver during initial set-up or intra-operatively in a manner that is safe for the patient and convenient for the clinician or user.

Moreover, instruments such as endoscopes may also have internal components such as optics and electronics that are sealed and create additional mass in a handle or housing at a proximal portion of the instrument. Economic considerations may make it desirable for the endoscope to survive repeated procedures, reprocessing, and sterilization cycles. In cases where insertion and retraction of the instrument shaft is driven by an instrument-based insertion architecture, where the instrument driver operates inputs on the removable tool to advance or retract the instrument shaft, it can be desirable to support added mass at the proximal end of such scopes to support cantilevered loads or reduce strength requirements of the endoscope shaft that contains sealed components.

Figure 16:
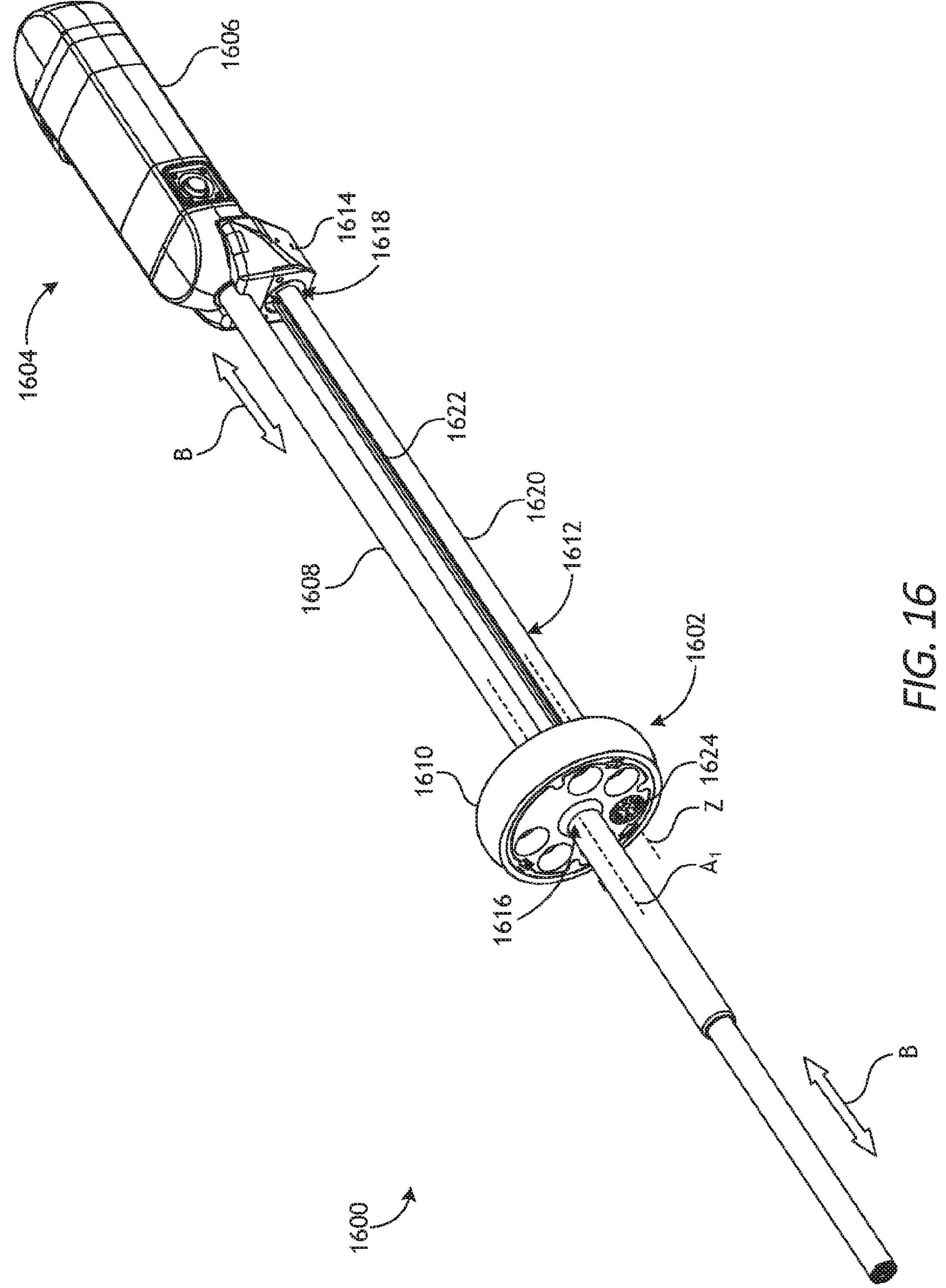
FIG. 16 is an isometric side view of a portion of an example robotic surgical system that may incorporate some or all of the principles of the present disclosure.

FIG. 16 is an isometric side view of a portion of an example robotic surgical system 1600 that may incorporate some or all of the principles of the present disclosure. The robotic surgical system 1600 (hereafter "the system 1600") may be similar in some respects to the robotically-enabled systems 100, 400, and 900 described herein with reference to FIGS. 1-13 and, therefore, may be used to undertake a variety of surgical operations or procedures, including any of the medical procedures discussed herein. As illustrated, the system 1600 includes an instrument mount 1602 and a medical instrument 1604 mountable to or otherwise matable with the instrument mount 1602.

The medical instrument 1604 (hereafter "the instrument 1604") can have any of a variety of configurations capable of performing one or more medical or surgical functions. In the illustrated embodiment, the instrument 1604 is an endoscope insertable into a patient to provide a view of an internal anatomical site within the patient, but various principles of this disclosure may be applied to any of a variety medical or surgical instruments, including instrument having elongate shafts designed for minimally invasive procedures.

As illustrated, instrument 1604 includes a handle having an instrument housing 1606 and an elongate shaft 1608 extending distally from the instrument housing 1606. The instrument 1604 can have any of a variety of configurations capable of performing a variety of surgical functions. In some embodiments, for instance, the shaft 1608 may be designed to be delivered through an anatomical opening, lumen, incision, or and/or trocar.

The shaft 1608 may be either flexible (e.g., having properties similar to an endoluminal endoscope) or rigid (e.g., having properties similar to a laparoscope) or contain a customized combination of both flexible and rigid portions. When designed for endoscopy, the distal end of the shaft 1608 may include a steerable or controllable bending section that may be articulated and bent.

According to some embodiments, electronic and/or optical components (not shown) such as circuit boards or fiber optic connectors may be housed in the instrument housing 1606 and designed to facilitate operation of the instrument 1604. Alternatively, or in combination, an internal actuation system may be housed within the instrument housing 1606 and designed to facilitate operation of the instrument 1604. In some embodiments, for example, the drive housing 1606 may include a plurality of drive members that extend within the shaft 1608 to its distal end. Selective actuation of one or more of the drive members may cause the shaft 1608 to bend and thereby direct the distal end of the shaft 1608 in a desired orientation. In other embodiments, selective actuation of one or more of the drive members may cause an end effector attached to the distal end of the shaft 1608 to articulate (pivot), or may cause the end effector to actuate (operate). According to some embodiments, a flexible cable (not shown in FIG. 16) is connected to the instrument housing 1606 and can be used to connect the instrument to a tower or support console of the surgical system. The cable can be used to provide power and/or transfer signal to or from the instrument. In some embodiments, for example, the cable may include optical and electrical cables used to transfer light to the endoscope for illuminating the surgical scene, power to and/or to transfer image data from the endoscope to the tower for further processing.

The instrument mount 1602 includes a base 1610, an elongate rail 1612 extending proximally from the base 1610, and a carriage 1614 mounted to the rail 1612 and able to traverse the rail 1612 upon actuation. As discussed below, the instrument housing 1606 may be mounted or otherwise releasably coupled to the carriage 1614 using various coupling and locking mechanisms that releasably couple the instrument 1604 to the carriage 1614. The base 1610 defines a central aperture 1616 through which a longitudinal axis $A_1$ extends. When the instrument 1604 is properly mounted to the instrument mount 1602, the shaft 1608 will penetrate the base 1610 at the central aperture 1616 and coaxially align with the longitudinal axis $A_1$.

The rail 1612 extends parallel to the longitudinal axis $A_1$ along an axis Z. The rail 1612 is selectively actuatable to move the carriage 1614 axially along the rail 1612 and the z-axis to correspondingly advance or retract the instrument 1604 and the shaft 1608 relative to the instrument mount 1602, as indicated by the arrows B. Actuating the rail 1612 can move the carriage 1614 from a fully retracted position, as shown in FIG. 16, to a fully extended position where the carriage 1614 is positioned adjacent to or in contact with the base 1610. As the carriage 1614 traverses the rail 1612 along the z-axis, the instrument 1604 and the shaft 1608 correspondingly move between the fully retracted and extended positions.

In some embodiments, the carriage 1614 is able to traverse the axial length of the rail 1612 by mechanical interaction with a carriage nut 1618 coupled to or forming part of the carriage 1614. In some embodiments, for example, the rail 1612 may comprise a rotatable lead screw 1622 that defines outer helical threading (not shown), and the carriage nut 1618 may be mounted to the rail 1612 and define internal helical threading (not shown) matable with the outer helical threading of the rail 1612. In such embodiments, rotation of the rail 1612 causes the carriage nut 1618 to convert the rotational force of the rail 1612 into an axial load applied to the carriage 1614, thus advancing or retracting the carriage 1614 along the length of the rail 1612. In the illustrated embodiment, the rail 1612 further comprises a shroud 1620 and the lead screw 1622 is rotatably mounted within the shroud 1620 and threadably matable with the carriage nut 1618. In operation, the lead screw 1622 is actuated to rotate relative to the shroud 1620 and thereby advance or retract the carriage 1608 and simultaneously advance or retract the instrument 1604 relative to the instrument mount 1602.

The rail 1612 may be made of a variety of rigid materials including, but not limited to, a plastic (e.g., an extruded polymer), a metal (e.g., aluminum, stainless steel, brass, etc.), a composite material (e.g., carbon fiber, fiberglass, etc.), or any combination thereof. The rail 1612 (or the lead screw 1622) may exhibit a surface finish or include a coating that reduces friction against the carriage nut 1618 when the carriage 1614 is under loading, e.g., twisting or compressive loads. In at least one embodiment, for instance, the outer helical threading of the rail 1612 (or the lead screw 1622) may be coated with a lubricant or lubricious substance, such as polytetrafluoroethylene (PTFE or TEFLON®). In other embodiments, or in addition thereto, the outer helical threading of the rail 1612 (or the lead screw 1622) may be anodized or otherwise exhibit an anodized outer surface.

As illustrated, the base 1610 may include a drive input 1624 operable by a drive output of the robotic system to move the carriage along the rail, such that the instrument shaft is advanced or retracted together with movement of the rail. According to some embodiments, for example as seen in FIG. 16, the drive input 1624 is a rotatable drive input that is actuatable to actuate (rotate) the rail 1612 (or the lead screw 1622), causing the carriage to translate along the rail. As described below, the drive input 1624 may be matable with a corresponding drive output of an instrument driver such that movement (rotation) of the drive output correspondingly moves (rotates) the drive input 1624 and thereby rotates the rail 1612. While only one drive input 1624 is depicted, more than one drive input may be included in the base 1610 to accommodate other functions of the instrument mount 1602 or the medical instrument 1604. Also, while a lead screw arrangement is described, other arrangements may use mechanisms such as, for example, rack gears, belts, pulleys, or cables to move the carriage along the rail.

The drive input 1624 may be operatively coupled to the rail 1612 such that rotation (actuation) of the drive input 1624 correspondingly rotates the rail 1612, which causes the carriage 1614 to advance or retract along the rail 1612 and simultaneously advances or retracts the instrument 1604 along the longitudinal axis $A_1$, depending on the rotational direction of the rail 1612. As used herein, the phrase "operatively coupled" refers to a coupled engagement, either directly or indirectly, where movement of one component causes corresponding movement of another component. With respect to the drive input 1624 being operatively coupled to the rail 1612, such operative coupling may be facilitated through intermeshed gears (not shown) arranged within the base 1610, but could alternatively be facilitated through other mechanical means, such as cables, pulleys, drive rods, direct couplings, etc., without departing from the scope of the disclosure.

Figure 17:
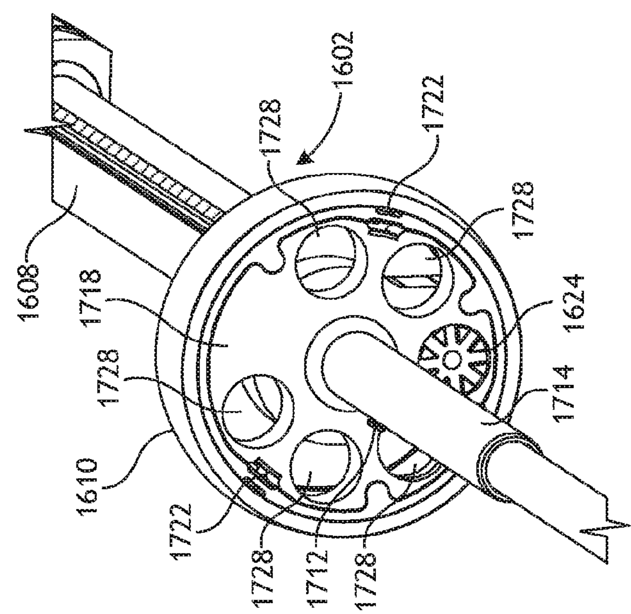
FIG. 17 is an enlarged isometric end view of the base of FIG. 16 and an example instrument driver, according to one or more embodiments.
Figure 17:
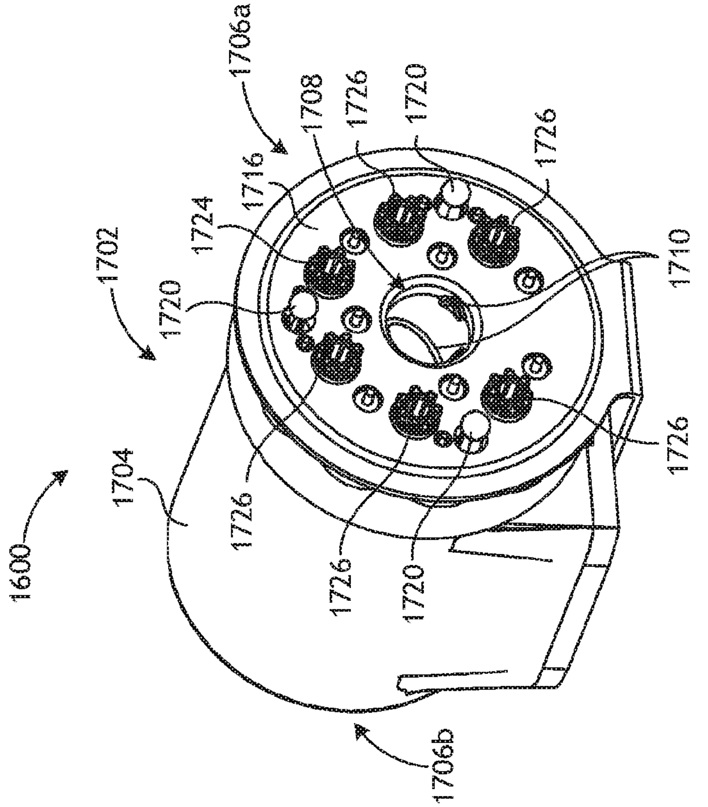

FIG. 17 depicts enlarged, isometric end views of the base 1610 and an example instrument driver 1702, according to one or more embodiments. The instrument driver 1702 may form part of the system 1600, and may be similar in some respects to the instrument drivers 1102, 1200 of FIGS. 11 and 12, respectively, and therefore may be best understood with reference thereto. Similar to the instrument drivers 1102, 1200, for example, the instrument driver 1702 may be mounted to or otherwise positioned at the end of a robotic arm (not shown) and designed to provide motive forces required to operate at least a portion of the instrument 1604 (FIG. 16). In a mounted configuration of the instrument 1604, the shaft 1608 of the instrument 1604 extends through and penetrates the instrument driver 1702.

The instrument driver 1702 has a body 1704 having a first or "proximal" end **1706*a* and a second or "distal" end 1706*b* opposite the first end 1706*a*. In the illustrated embodiment, the first end 1706*a* of the instrument driver 1702 is matable with and releasably coupled to the base 1610, and the shaft 1608 extends through the body 1704 and distally from the second end 1706*b*. More specifically, the shaft 1608 can penetrate the instrument driver 1702 by extending through a central aperture 1708 defined longitudinally through the body 1704 between the first and second ends 1706*a,b***.

To align the base 1610 with the instrument driver 1702 in a proper angular orientation, one or more alignment guides 1710 may be provided or otherwise defined within the central aperture 1708 and configured to engage one or more corresponding alignment features 1712 provided on the base 1610. In the illustrated embodiment, the alignment feature 1712 comprises a protrusion or projection defined on or otherwise provided by an alignment nozzle 1714 extending distally from the base 1610. In one or more embodiments, the alignment guide(s) 1710 may include a curved or arcuate shoulder or lip configured to receive and guide the alignment feature 1712 as the alignment nozzle 1714 enters the central aperture 1708. As the alignment feature(s) 1712 slides along the alignment guide(s) 1710 in the distal direction, the base 1610 will be oriented to a proper angular alignment with the instrument driver 1702. In other embodiments, the alignment nozzle 1714 may be omitted and the alignment feature(s) 1712 may alternatively be provided on the shaft 1608, without departing from the scope of the disclosure.

As illustrated, a drive interface 1716 is provided at the first end **1706*a* of the instrument driver 1702, and a driven interface 1718 is provided on the base 1610. The drive and driven interfaces 1716, 1718 may be configured to mechanically, magnetically, and/or electrically couple the base 1610 to the instrument driver 1702. To accomplish this, the drive and driven interfaces 1716, 1718 may provide one or more matable locating features configured to secure the base 1610 to the instrument driver 1702. In the illustrated embodiment, for example, the drive interface 1716 provides one or more interlocking features 1720 (three shown) configured to locate and mate with one or more complementary-shaped pockets 1722 (two shown, one occluded) provided on the driven interface 1718. The features 1720 may be configured to align and mate with the pockets 1722 via an interference or snap fit engagement, for example. As will be appreciated, other types or configurations of mating features may be provided to mate the base 1610 to the instrument driver 1702**, without departing from the scope of the disclosure.

The instrument driver 1702 includes one or more drive outputs that mate with the drive input 1624 provided on the base 1610. In some embodiments, as illustrated, the drive output 1724 may define splines or features designed to mate with corresponding splined receptacles of the drive input 1624. The drive output 1724 may be configured to mate with the drive input 1624 directly or indirectly, for example, through an intermediate drive coupler of a sterile adapter. Once properly mated, the drive input 1624 may share an axis of rotation with the drive output 1724 to allow the transfer of rotational torque from the drive output 1724 to the drive input 1624. In some embodiments, the drive output 1724 may be spring loaded and otherwise biased to spring outwards away from the drive interface 1716. Moreover, the drive output 1724 may be capable of partially or fully retracting into the drive interface 1716.

In some embodiments, as depicted, the instrument driver 1702 may include one or more additional drive outputs 1726 (five shown) configured to mate with one or more additional drive inputs of the base 1610 to help undertake one or more additional functions of the instrument mount 1602 or the instrument 1604 (FIG. 16). In the illustrated embodiment, the base 1610 does not include additional drive inputs matable with the additional drive outputs 1726. Instead, the driven interface 1718 defines corresponding recesses or apertures 1728 configured to receive the additional drive outputs 1726. In other applications, however, additional drive inputs could be included in the base 1610 to mate with the additional drive outputs 1726, or the instrument mount 1602 might be replaced with another instrument mount having additional drive inputs, which would be driven by the additional drive outputs 1726.

In some embodiments, an instrument sterile adapter (ISA) may be placed at the interface between the instrument driver 1702 and the base 1610. In such applications, the interlocking features 1720 may operate as alignment features and possible latches for the ISA to be placed, stabilized, and secured. Stability of the ISA may be accomplished by a nose cone feature provided by the ISA and extending into the central aperture 1708 of the instrument driver 1702. Latching can occur either with the interlocking features 1720 or at other locations at the interface. In some cases, the ISA will provide the means to help align and facilitate the latching of the instrument 1604 to the ISA and simultaneously to the instrument driver 1702.

Medical instruments, such as the instrument 1604 of FIG. 16, can sometimes include a cable attached thereto and otherwise extending from the back (proximal end) of the instrument. The cable serves several functions. In some applications, for example, the cable can contain optical, electrical, and/or fluidic lines (wires) for transferring optical and electrical signals and fluids between the instrument (e.g., an endoscope) and an adjacent tower (e.g., the tower 112 of FIG. 1) or another external device. The cable can further supply electrical power to the instrument. The cable typically includes a strain relief coupled to the instrument to help mitigate strain and fatigue on the internal components of the cable during operation. As used herein, the term "cable" may refer to one or multiple lines of cabling. Further, the term cable may encompass multiple lines of cabling arranged in parallel, in series, or both. For example, the term cable may encompass multiple lines of cabling connected together in series via sockets or other separable connections. Additionally or alternatively, a cable may encompass multiple lines of cabling housed together within a single outer jacket. A cable may also encompass various combinations thereof, where the arrangement of cabling changes at different locations along the length of the cable.

The size of the various internal components and/or strain reliefs for an instrument, such as an endoscope, may lead to sacrifices in working length due to the excessive size of the handle section. Since the cable may contain relatively heavy or bulky optical and electrical cables, in robotic use, the weight and bulk of the cable can lead to problematic moment reactions on the corresponding robotic arm. According to some embodiments, the cable for an endoscope or other instrument may be redirected internally or externally to the handle of the device.

Figure 18A:
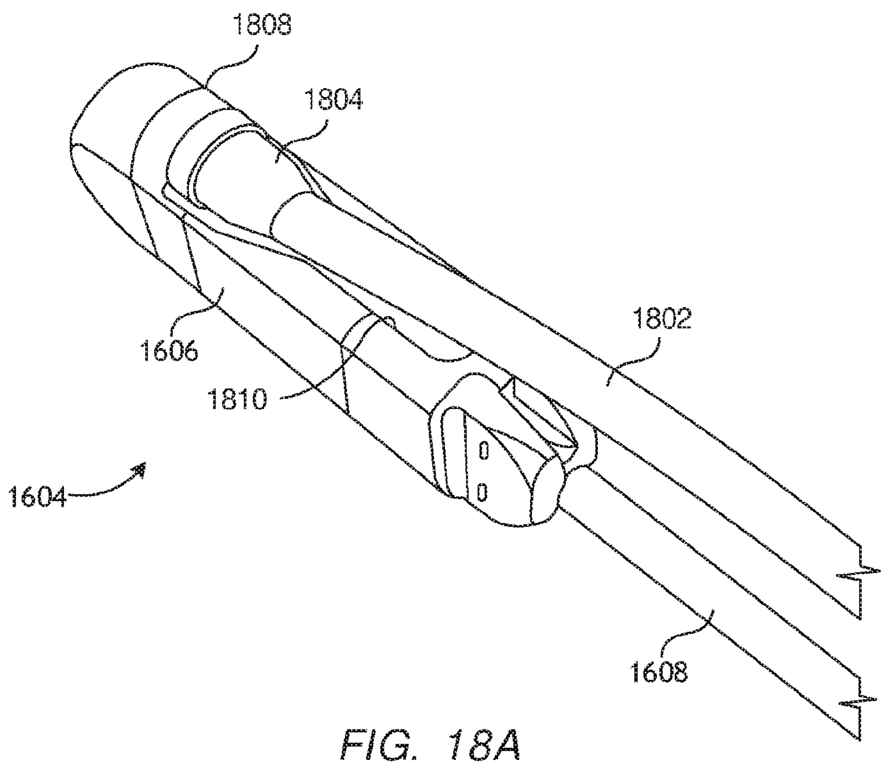
FIGS. 18A and 18B are isometric and side views, respectively, of one example of the instrument of FIG. 16, according to one or more embodiments.
Figure 18B:
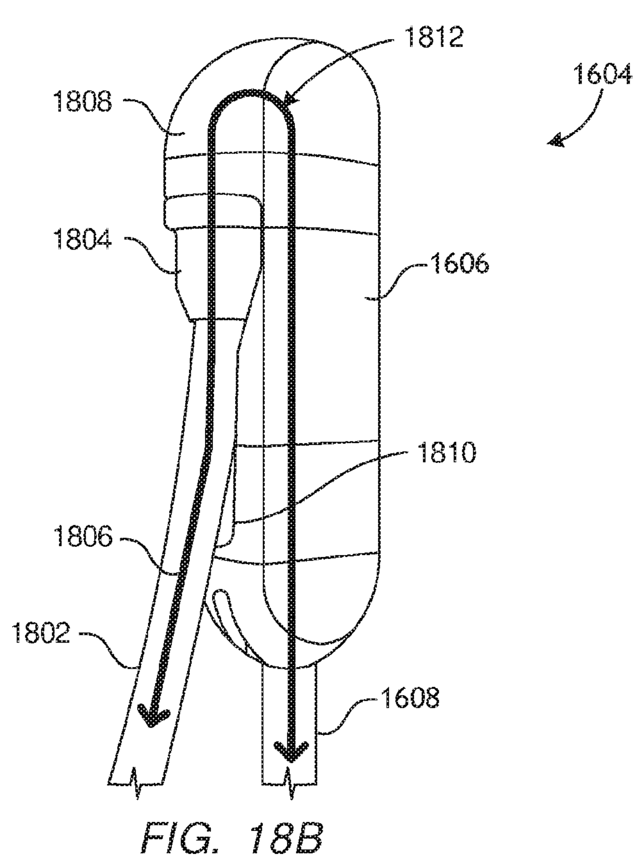

FIGS. 18A and 18B are isometric and side views, respectively, of one example of the instrument 1604 of FIG. 16, according to one or more embodiments. More specifically, FIGS. 18A-18B depict the instrument housing 1606 and the shaft 1608 extending distally from the instrument housing 1606. The instrument 1604 may further include a cable 1802 penetrating (exiting or entering) the housing 1606 at a strain relief 1804 secured to the housing 1606. In some embodiments, however, the strain relief 1804 may be omitted.

The cable 1802 may extend between the instrument 1604 and an adjacent tower (e.g., the tower 112 of FIG. 1) or another type of external device configured to support operation of the instrument 1604. The cable 1802 may contain (house) several types of lines, wires, or conduits, collectively referred to herein as internal components 1806 (FIG. 18B) of the cable 1802. The internal components 1806 may be configured to communicate various signals and/or substances to/from the instrument 1604 and/or an end effector arranged at a distal end of the instrument 1604. Example internal components 1806 include, but are not limited to, an optical line (conduit) for transferring optical signals, an electrical line for transferring electrical signals and/or power, a fluidic line for conveying fluids, or any combination thereof. According to some embodiments, the cable 1802 may include multiple lines housed together in a single jacket in a portion of the cable that is external to the housing 1606. The multiple lines may then separate or split, such that they are not housed in a single jacket, in a portion of the cable that is within the housing 1606. For example, an optical and electrical line may be housed in a single jacket in a portion of the cable external to the housing, then the optical and electrical lines may be split apart and be redirected in the internal portion of the housing 1606 in order to connect to convey separate electrical signals and optical signals to different portions of the instrument shaft.

As illustrated, the cable 1802 may penetrate (exit or enter) the housing 1606 along one lateral side of the housing 1606 and extend from the housing 1606 distally and otherwise in the same longitudinal direction as the shaft 1608. In some embodiments, a protuberance 1808 may be defined or otherwise provided on the side of the housing 1606 to receive the cable 1802. The protuberance 1808 may extend laterally past the side of the housing 1606 to a distance sufficient to accommodate the cable 1802 and the strain relief 1804 (if included). In some embodiments, a channel or groove 1810 may also be defined on the side of the housing 1606 and configured to accommodate, receive, or seat portions of the strain relief 1804 and/or the cable 1802. The cable 1802 may be configured so that it is naturally biased in a position along the lateral side of the housing 1606, but sufficiently flexible so that it can be lifted away from the lateral side during cleaning processes. The groove 1810 may prove advantageous in helping to achieve an ergonomic overall dimension when the instrument 1604 is handheld, as discussed in more detail below.

As schematically illustrated in FIG. 18B, the internal components of the cable 1802 may form a redirection 1812 within the housing 1606 and extend along (within) the shaft 1608. In some embodiments, the redirection 1812 may comprise a 180° bend of the internal components 1806 of the cable 1802. FIG. 18B also illustrates how a line or lines of the cable may extend to convey signals, illumination, or substances to the instrument shaft 1608. In an endoscope, it may be useful to convey both light and electrical signals to or from the endoscope via the cable. For example, a camera arranged at the distal end of the endoscope shaft can receive power or control signals for operation, or provide image data to an external processor in the tower for further processing or presentation on an external display. Additionally or alternatively, light can be piped in from the external illumination source via optical fibers to convey light to the distal end of the shaft to illuminate the surgical scene. According to some embodiments, both such light and electrical signals may be conveyed between the endoscope and the tower via the cable 1802, with a redirection 1812 in the housing 1606 to allow these lines to extend in or otherwise connect to components in the distally extending shaft 1608.

As compared to conventional medical instruments, where the cable extends out the back (proximal) end of the housing, having the cable 1802 penetrate the housing 1606 on the side and including the redirection 1812 may provide several benefits. For example, the elimination or reduction of a strain relief and cable exit from the rear of the housing 1606 increases the length to an endoscope that can be appropriated to the shaft 1608 under the size limitations of a sterilization tray, thus increasing the working length of the endoscope. Additionally or alternatively, the redirection 1812 can shift the mass of the cable 1802 and thereby reduce the moment on the robot arm by 30% or more, in some embodiments. Additionally or alternatively, the elimination or reduction of a strain relief and cable exit from the rear of the housing 1606 minimizes the risk of collisions with adjacent robotic arms.

Figure 19:
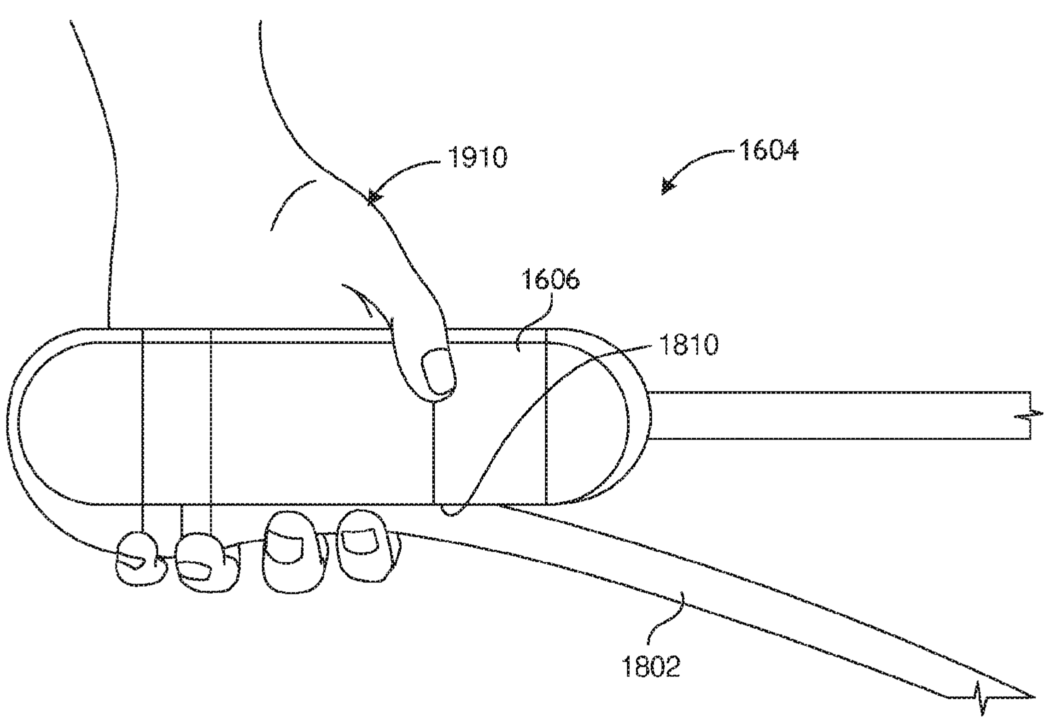
FIG. 19 is a side view of a hand-held version of the instrument of FIG. 16, according to one or more embodiments.

FIG. 19 is a side view of a hand-held version of the instrument 1604, according to one or more embodiments. As illustrated, a user (e.g., a surgeon, a technician, a nurse, etc.) may be able to grasp the housing 1606 with a hand 1910, and the groove 1810 may help achieve an ergonomic overall dimension that allows the cable 1802 to be tightly seated against the housing 1606. During handheld use, the redirection 1812 can help provide a compact form factor that is comfortable to hold and leads to improved usability of the instrument 1604. As seen in FIG. 19, because the cable extends along a lateral side of the housing 1606, the cable 1802 can be gripped by the hand 1910 together with the housing during manual use. Further, because the cable 1802 exits the housing from a lateral side, as opposed to the distalmost end of the housing, the cable can bend away from the instrument shaft near the distal end of the housing to improve the usable length of the instrument.

Figure 20:
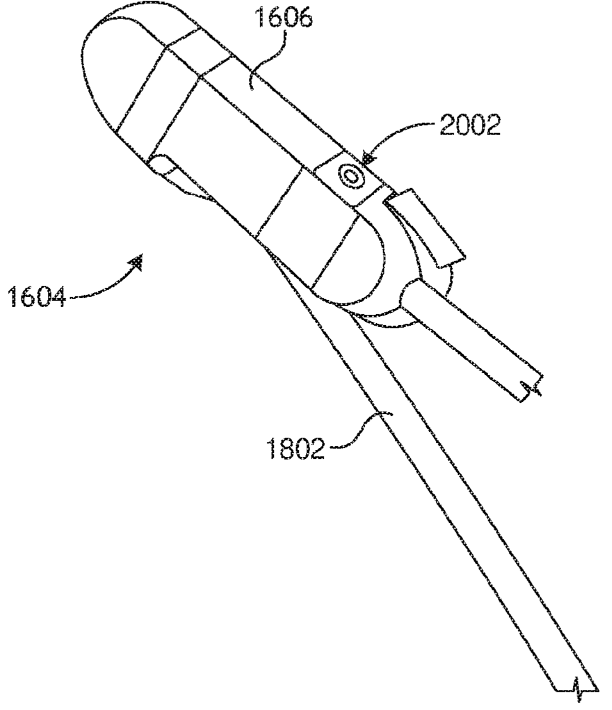
FIG. 20 is an isometric view of another hand-held version of the instrument of FIG. 16, according to one or more additional embodiments.

FIG. 20 is an isometric view of another hand-held version of the instrument 1604, according to one or more additional embodiments. The illustrated instrument may be configured for both manual control (e.g., via hand-held operation like shown in FIG. 19) and robotic control (e.g., via the instrument mount 1602 shown in FIGS. 16 and 17). In some embodiments, as illustrated, the instrument 1604 may include a manual input button 2002 provided on the housing 1606. In at least one embodiment, the cable 1802 may penetrate the housing 1606 on one lateral side of the housing 1606, and the button 2002 may be provided on an opposite lateral side of the housing 1606. The button 2002 may serve various functions. In one embodiment, for example, the button 2002 may be manually actuated for image capture. In another embodiment, or in addition thereto, the button 2002 may be manually actuated for handheld endoscope operation. Moreover, while only one button 2002 is depicted, it is contemplated herein to include multiple buttons 2002 on the lateral side of the housing. Further, while illustrated as a button, in various embodiments the manual input can take the form of any manually operable or actuatable device, such as a lever, slider, wheel, or touch sensor, to permit manual or finger-operated actuation of a function of the device.

Figures 21A, 21B, 21C:
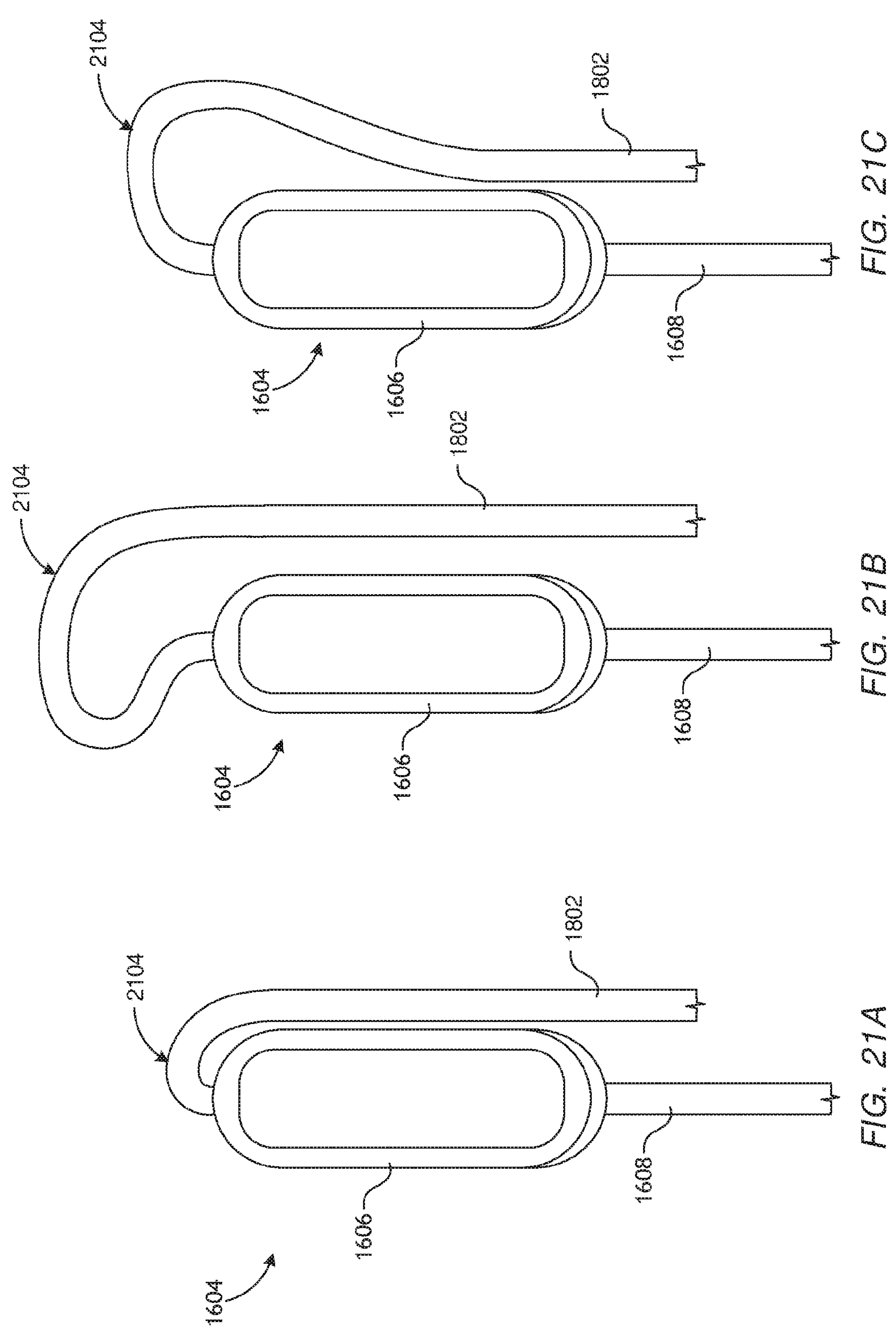
FIGS. 21A-21C are schematic diagrams of examples of the instrument of FIG. 16, according to various additional embodiments.

FIGS. 21A-21C are schematic diagrams of examples of the instrument 1604, according to various additional embodiments. As illustrated, the instrument 1604 includes the shaft 1608 extending distally from the housing 1606. The instrument 1604 further includes the cable 1802 extending from a proximal (rear) end of the housing 1606. In some embodiments, as illustrated, the cable 1802 may be exposed and otherwise not capped with a strain relief (e.g., the strain relief 1804 of FIGS. 20A-20B). In other embodiments, however, an appropriate strain relief may be included at the proximal end 2303 to protect the cable 1802 from strain and/or fatigue, without departing from the scope of the disclosure.

As illustrated, the cable 1802 may extend distally from the housing 1606 and otherwise in the same direction as the shaft 1608 after forming a redirection 2104 external to the housing 1606. The redirection 2104 may comprise at least a 180° bend in the cable 1802 to enable to cable 1802 to extend distally along shaft 1608. It is contemplated herein that the external redirection 2104 may take on various forms, some more efficient than others.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical system, comprising:

an instrument mount arrangeable at a distal end of a robotic arm;

an endoscope comprising a shaft and a housing having a distal-facing surface, wherein the housing is configured to be mounted to the instrument mount, and the shaft extends from the housing in a distal direction;

a cable connected to the housing and extending from the distal-facing surface in the distal direction and along a lateral side of the housing wherein the cable comprises an optical line and an electrical line, the optical line is configured to transmit light between the endoscope and an external illumination source, and the electrical line is configured to transmit electrical signals between the endoscope and an external processor.

2. The robotic surgical system of claim 1, wherein the cable is redirected 180 degrees within the housing of the endoscope.

3. The robotic surgical system of claim 1, wherein the cable is positioned in a groove along the lateral side of the housing.

4. The robotic surgical system of claim 1, wherein the endoscope comprises a manual input positioned on a side of the housing opposite the lateral side of the housing.

5. The robotic surgical system of claim 4, wherein the manual input is a button.

6. The robotic surgical system of claim 1, wherein the instrument mount comprises a carriage configured to receive the housing, wherein the carriage is actuatable to advance or retract the endoscope when the housing of the endoscope is received in the carriage.

7. The robotic surgical system of claim 6, wherein the instrument mount further comprises a base having a drive input configured to removably couple to a drive output of an instrument driver of the robotic arm, wherein the drive input is actuatable by the drive output to advance or retract the carriage.

8. The robotic surgical system of claim 6, wherein the carriage is mounted to a lead screw that is rotatable to advance or retract the carriage.

* * * * *